US00PP14584P29

(12) United States Plant Patent
Schräder

(10) Patent No.: US PP14,584 P2
(45) Date of Patent: Mar. 9, 2004

(54) VARIETY OF VERBENA PLANT NAMED 'SUMVERB 02'

(50) Latin Name: *Verbena hybrid*
Varietal Denomination: Sumverb 02

(75) Inventor: Ralf Schräder, Lüdinghausen (DE)

(73) Assignee: Grunewald Veredlings B.V. (NL)

( * ) Notice: Subject to any disclaimer, the term of this patent is extended or adjusted under 35 U.S.C. 154(b) by 0 days.

(21) Appl. No.: 10/378,478

(22) Filed: Mar. 3, 2003

(51) Int. Cl.[7] ..... A01H 5/00
(52) U.S. Cl. ..... Plt./308
(58) Field of Search ..... Plt./308

*Primary Examiner*—Bruce R. Campell
*Assistant Examiner*—Susan B. McCormick
(74) *Attorney, Agent, or Firm*—Webb Ziesenheim Logsdon Orkin & Hanson, P.C.

(57) ABSTRACT

A new and distinct early flowering Verbena plant with violet colored flowers.

2 Drawing Sheets

Botanical classification: Verbena hybrid.
Varietal denomination: 'Sumverb 02'.

BACKGROUND OF THE INVENTION

The present invention comprises a new and distinct cultivar of Verbena plant known by the varietal name 'Sumverb 02'. The new variety was discovered in August 2001 in a selected breeding program in Lüdinghausen, Germany designed to produce a new variety of Verbena with a hanging character and great flowers. The new variety was selected from a cross of proprietary unpatented breeding plants Seedling 26 (female parent) and Seedling 47 (male parent). The new variety is a hanging habitus similar to its parents, but has a larger flower size than both parents. The new variety has a hanging character similar to 'Temari Violet', but 'Temari Violet' (unpatented) has 81A colored flowers and 'Sumverb 02' has 87A colored flowers. The new variety was first asexually reproduced in October 2001 by cuttings in Lüdinghausen, Germany. The new variety has been trial and field tested at Lüdinghausen and has been found to retain its distinctive characteristics and remain true to type through successive propagations.

The following trait distinguishes 'Sumverb 02' as a new and distinct cultivar:

1. Flower color.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
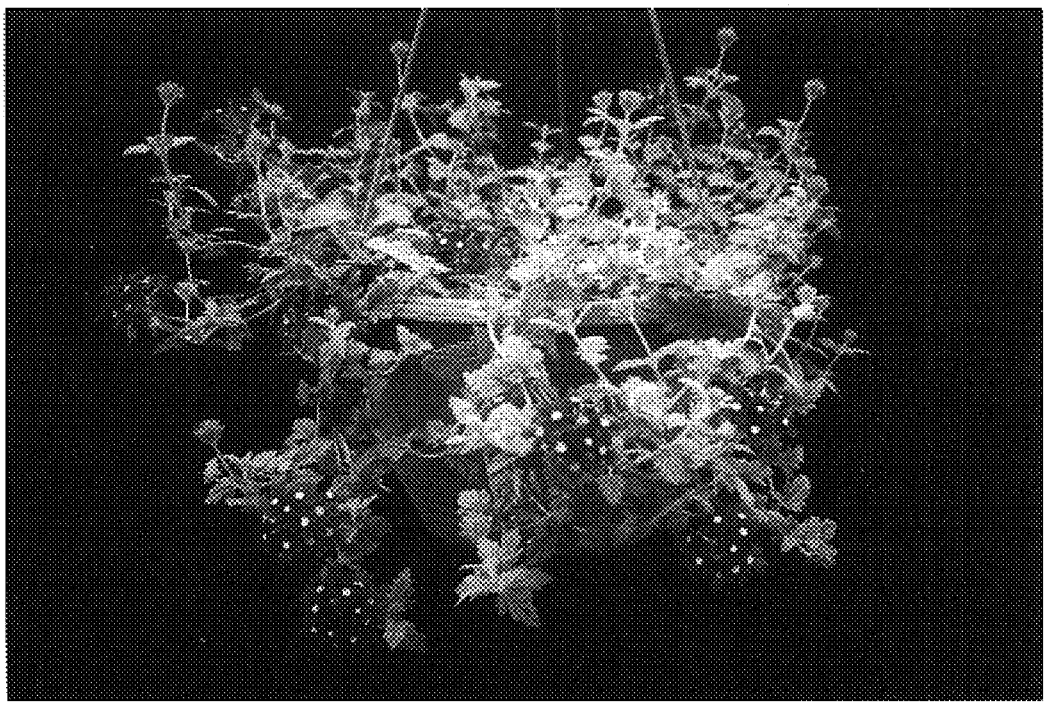
FIG. 1 is a photograph of the plant.
Figure 2:
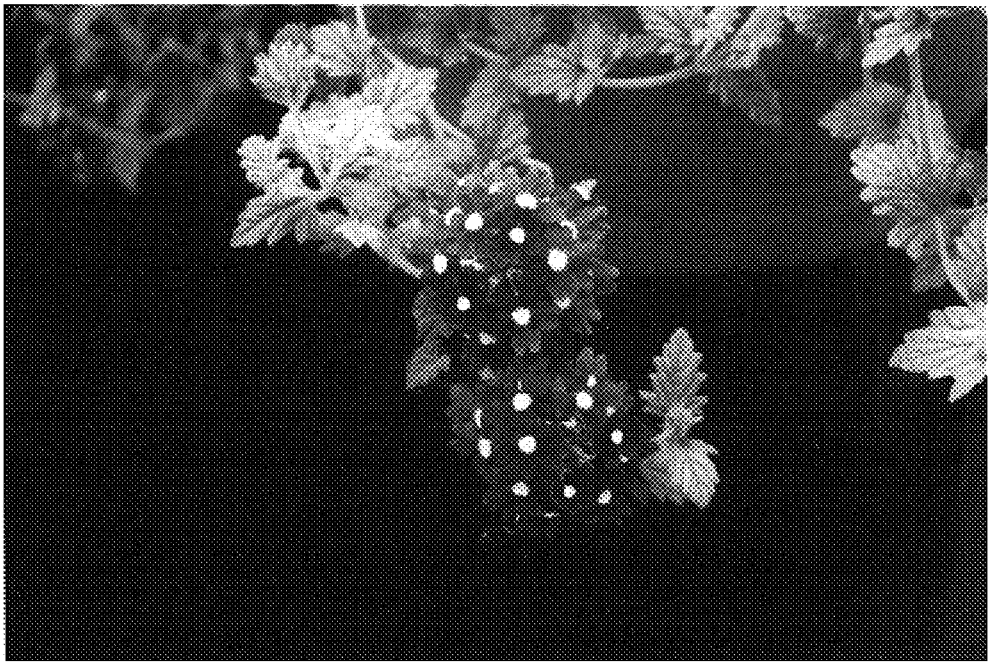
FIG. 2 is a close up view of the blossoms of the new plant.

The following detailed description sets forth characteristics of the new cultivar. The data which defines these characteristics were collected by asexual reproductions by cuttings carried out in Lüdinghausen, Germany. Plants for the description were 8 weeks old, grown in a greenhouse in 11 cm containers at 16° C. temperature. The color readings were taken in a greenhouse under sunny natural light. Color references are primarily to the 2001 R.H.S. Colour Chart of The Royal Horticultural Society of London.

PLANT

Form: Mounded.
Height (from soil to top of flowers): 25 cm.
Diameter: 35–45 cm.
Vigor: Medium.
Roots:
- *Habit.*—Spreading.
- *Time to initiate roots.*—6 days at 16° C.
- *Time to develop roots.*—10 days at 16° C.

Time to finish a flowered plant: About 8 weeks in a 11 cm container.
Branching habit: Hanging; good; from every node.
Lateral branches:
- *Color.*—144B.
- *Texture.*—Pubescent.
- *Diameter.*—1 mm.
- *Internode length.*—40 mm.

Foliage:
- *Arrangement.*—Single.
- *Size of leaf.*—Length: 24 mm. Width: 20 mm.
- *Shape of leaf.*—Lanceolate.
- *Shape of apex.*—Obtuse.
- *Shape of base.*—Truncate.
- *Texture.*—Pubescent.
- *Aspect.*—Flat.
- *Margin.*—Crenate.
- *Color.*—Young leaves: Upper surface: 143C. Lower surface: 143A. Mature leaves: Upper surface: 137C. Lower surface: 139A.
- *Petiole.*—Length: 1 mm. Diameter: 1 mm. Color: 139C.
- *Veins.*—Venation type: Pinnate. Color: Upper surface: 139D. Lower surface: 144C.

FLOWER

Natural flowering season: Spring to Autumn.
Bud (at one day before opening):
- *Shape.*—Long; 5 parted.
- *Diameter.*—2 mm.
- *Length.*—12 mm.
- *Color.*—N89A.

Corymb:

*Number of flowers per corymb.*—20.

*Diameter.*—Approximately 50 mm.

*Length.*—Approximately 40 mm.

Corolla:

*Form.*—Fused petals.

*Petals/1obes.*—Number: 5 Length: Approximately 9 mm. Width: Approximately 8 mm. Shape: Obovate. Aspect: Flat. Margin: Entire. Texture and appearance: Smooth. Color: When opening: Upper surface: 86B. Lower surface: 86A. Fully opened: Upper surface: 86C. Lower surface: N87A.

*Throat.*—Color: 1C. Texture: Pubescent.

*Tube color.*—1C.

Calyx:

*Form.*—Fused at base; cylindrical.

*Length.*—15 mm.

*Diameter.*—1 mm.

*Sepal shape.*—Cylindrical; 5 connected sepals.

*Sepal margin.*—Acuminate.

*Sepal texture.*—Pubescent.

*Sepal color.*—Upper surface: 147B. Lower surface: 147C.

Disease resistance: No resistance to diseases noted to date.

Fragrance: Lightly fragrant.

Temperature tolerance: From 0.5° C. to 45° C.

REPRODUCTIVE ORGANS

Stamens:

*Number.*—3.

*Filament length.*—0.5 mm.

*Anthers.*—Shape: Oval. Length: 0.2 mm. Color: 1B.

*Pollen.*—Color: 1B. Amount: Moderate.

Pistil:

*Length.*—12 mm.

*Style.*—Length: 1 mm. Color: 141D.

*Stigma.*—Shape: Oval. Color: 142A.

Seed production: None.

I claim:

1. A new and distinct variety of Verbena plant substantially as shown and described.

* * * * *